US00PP09390P

United States Patent [19]

Christensen

[11] Patent Number: Plant 9,390

[45] Date of Patent: Dec. 5, 1995

[54] HYBRID TEA ROSE PLANT NAMED 'JACYES'

[75] Inventor: Jack E. Christensen, Ontario, Calif.

[73] Assignee: Bear Creek Gardens, Inc., Medford, Oreg.

[21] Appl. No.: 327,007

[22] Filed: Oct. 21, 1994

[51] Int. Cl.[6] ..... A01H 5/00

[52] U.S. Cl. ..... Plt./15

[58] Field of Search ..... Plt./15

[56] References Cited

U.S. PATENT DOCUMENTS

P.P. 4,847 5/1982 Warriner ..... Plt./15

P.P. 8,706 5/1994 Christensen ..... Plt./15

*Primary Examiner*—Howard J. Locker

*Attorney, Agent, or Firm*—Klarquist Sparkman Campbell Leigh & Whinston

[57] ABSTRACT

A Hybrid Tea rose plant having strong, vigorous, upright, well branched growth habit, dark green, glossy, mildew resistant foliage, bright, non-fading yellow flowers, and moderate fragrance.

1 Drawing Sheet

The present invention relates to a new and distinct variety of rose plant of the Hybrid Tea class which was originated by me by crossing two unnamed seedlings.

The primary objective of this breeding was to produce a new rose variety having the excellent vigor and dark green foliage of the female seedling, combined with the bright yellow, broad petals and vigor of the male parent. The objective was substantially achieved, along with other desirable improvements, as evidenced by the following unique combination of characteristics that are outstanding in the new variety and that distinguish it from its parents, as well as from all other varieties of which I am aware:

1. Strong, vigorous, upright, well branched growth habit;
2. Dark green glossy, mildew resistant foliage;
3. Bright, non-fading yellow flowers; and
4. Moderate fragrance.

Asexual reproduction of this new variety by budding, as performed as Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—Rosa hybrida.

*Commercial.*—Hybrid Tea.

FLOWER

Observations made from specimens grown in a garden environment at Somis, Calif.

Blooming habit: Recurrent.

Bud:

*Size.*—1½ inches long when the petals start to unfurl.

*Form.*—The bud form is long, pointed ovoid.

*Color.*—When sepals first divide bud color is Yellow Group 13A. When half blown, the upper sides of the petals are Yellow Group 13A; and the lower sides of the petals are Yellow Group 13A.

*Sepals.*—Color: Green Group 138C. Surface texture: Covered in fine hairs. There are three lightly appendaged sepals. There are two unappendaged sepals with hairy edges.

*Receptacle.*—Color: Green Group 141C. Shape: Funnel. Size: Medium (⅜ inch ×¼ inch). Surface: Smooth:

*Peduncle.*—Length: Medium. Surface: Smooth, with some glands. Color: Bronzy. Strength: Stiff, erect.

Bloom:

*Size: Large. Average open size is* 4½ inches.

*Borne.*—Singly.

*Stems.*—Medium. Average length is about 18 inches to 22 inches.

*Form.*—When first open: High centered. Permanence: Retains its form to the end, outer petal edges curl slightly.

*Petalage.*—Number of petals under normal conditions: 25.

*Color.*—The upper side of the petals is Yellow Group 13A. The reverse side of each petal is Yellow Group 13A. The color of the base of petals is Yellow Group 13A. The major color on the upper side is Yellow Group 13A.

*Variegations.*—None.

*Discoloration.*—The general tonality at the end of the first day: No change. At the end of the third day, no change. Excellent yellow color through the fifth day. Some fading at petal drop to Yellow Group 13B. at the sixth or seventh day.

*Fragrance.*—Moderate.

Petals:

*Texture.*—Thick, leathery.

*Shape.*—Round.

*Form.*—Tips slightly recurved, edges slightly wavy.

*Arrangement.*—Imbricated, with a few petaloids in the center.

*Persistence.*—Drop off cleanly.

*Lastingness.*—On the plant: Fair ( 6 to 7 days). As a cut flower: Fair (7 to 8 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Color: Greenish white.

Form: Bush.

Growth: Vigorous, upright, branching.

Foliage:

*Number of leaflets on normal mid-stem leaves.*— 5 or 7.

*Size.*—Large (6½ inches × 4½ inches).

*Quantity.*—Abundant.

*Color.*—New foliage: Greyed Red Group 178B. Old foliage: Green Group 138A on upper side, and Green Group 139B on lower side.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Smooth with an occasional prickle.

*Stipules.*—Long (1 inch), serrated.

*Disease resistance.*—Resistant to mildew under normal growing conditions at Somis, Calif.

Wood:

*New wood.*—Color: Reddish. Bark: Smooth.

*Old wood.*—Color: Green, except when exposed to strong sunlight, when it is red. Bark: Smooth.

Prickles:

*Quantity.*—On main canes from base: Ordinary: On laterals from main canes: Ordinary.

*Form.*—Medium (⅜ inch), hooked downward.

*Color when young.*—Red.

Small prickles:

*Quantity.*—On main stalks: Few. On laterals: Few.

*Color.*—Red when young, then brown.

I claim:

1. A new and distinct variety of rose plant of the Hybrid Tea class, substantially as herein shown and described, characterized particularly as to novelty by the unique combination of its strong, vigorous, upright, well branched growth habit, dark green, glossy, mildew resistant foliage, bright non-fading yellow flowers, and moderate fragrance.

* * * * *

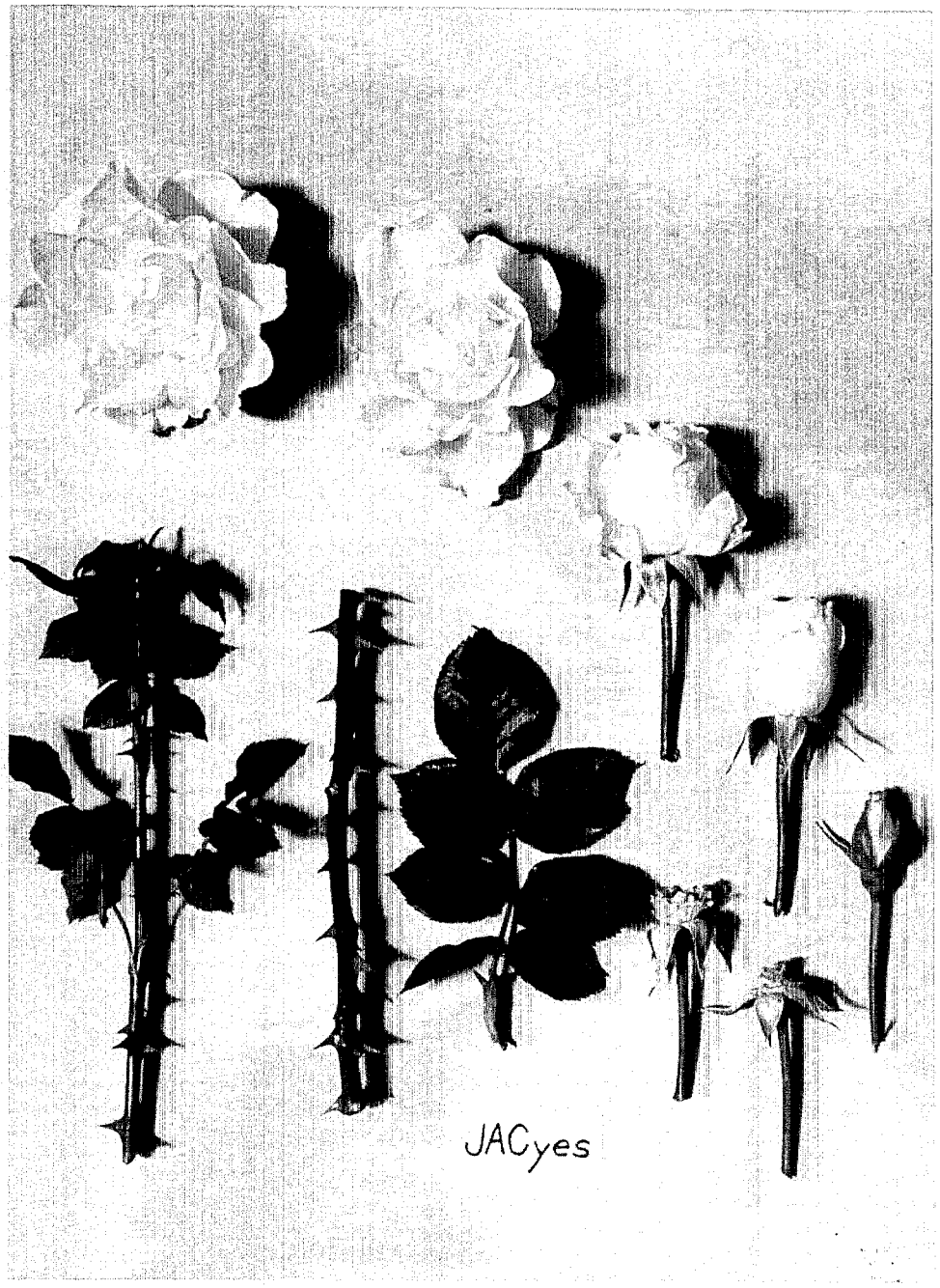
JACyes

UNITED STATES PATENT AND TRADEMARK OFFICE

CERTIFICATE OF CORRECTION

PATENT NO. : Plant 9,390

DATED : December 5, 1995

INVENTOR(S) : Jack E. Christensen

It is certified that error appears in the above-indentified patent and that said Letters Patent is hereby corrected as shown below:

Column 3, line 19, "138A on upper" should read --139A on upper--.

Signed and Sealed this

Sixteenth Day of July, 1996

*Attest:*

Bruce Lehman

BRUCE LEHMAN

*Attesting Officer*

*Commissioner of Patents and Trademarks*